United States Patent [19]
Lemelson

[11] Patent Number: 5,919,135
[45] Date of Patent: Jul. 6, 1999

[54] SYSTEM AND METHOD FOR TREATING CELLULAR DISORDERS IN A LIVING BEING

[76] Inventor: Jerome Lemelson, 930 Tahoe Blvd., Suite 286, Incline Village, Nev. 89541-9436

[21] Appl. No.: 08/807,646

[22] Filed: Feb. 28, 1997

[51] Int. Cl.$^6$ ........................................................ A61B 6/00
[52] U.S. Cl. ................................ 600/407; 604/4; 604/52; 600/419; 600/420; 600/408; 378/4
[58] Field of Search ...................................... 600/407, 408, 600/410, 411, 419, 420, 432, 433, 436, 437, 3–5; 128/920, 925; 604/4, 19, 27, 28, 30, 35, 36, 48, 49, 51, 52, 53; 607/901; 378/4

[56] References Cited

U.S. PATENT DOCUMENTS

| | | |
|---|---|---|
| 4,665,897 | 5/1987 | Lemelson . |
| 4,674,480 | 6/1987 | Lemelson . |
| 4,764,359 | 8/1988 | Lemelson . |
| 4,845,552 | 7/1989 | Jaggi et al. . |
| 4,867,742 | 9/1989 | Calderon . |
| 4,930,516 | 6/1990 | Alfano et al. . |
| 4,978,332 | 12/1990 | Luck et al. . |
| 5,366,440 | 11/1994 | Fossel . |
| 5,389,069 | 2/1995 | Weaver . |
| 5,405,919 | 4/1995 | Keefer et al. . |
| 5,464,013 | 11/1995 | Lemelson . |
| 5,466,576 | 11/1995 | Schulz et al. . |
| 5,489,508 | 2/1996 | West et al. . |
| 5,494,036 | 2/1996 | Uber, III et al. . |
| 5,500,346 | 3/1996 | Bright et al. . |
| 5,507,287 | 4/1996 | Palcic . |
| 5,512,443 | 4/1996 | Schlom et al. . |
| 5,545,667 | 8/1996 | Wiersema et al. . |
| 5,573,506 | 11/1996 | Vasko . |
| 5,579,767 | 12/1996 | Prince . |
| 5,609,153 | 3/1997 | Dumoulin et al. . |
| 5,643,203 | 7/1997 | Beiser et al. . |
| 5,685,989 | 11/1997 | Krivitski et al. . |
| 5,697,899 | 12/1997 | Hillman et al. . |

OTHER PUBLICATIONS

Weinberg, Robert A. "How Cancer Arises," Scientific American: Sep. 1996, pp. 62–70.
Sidransky, David. "Advances in Cancer Detection," Scientific American: Sep. 1996, pp. 104–109.
Greenwald, Peter. "Chemoprevention of Cancer," Scientific American. Sep. 1996, pp. 96–99.
Ruoslahti, Erkki. "How Cancer Spreads," Scientific American: Sep. 1996, pp. 72–77.

(List continued on next page.)

*Primary Examiner*—Marvin M. Lateef
*Assistant Examiner*—Shawna J. Shaw
*Attorney, Agent, or Firm*—Niro,Scavone,Haller & Niro

[57] ABSTRACT

A system and method is provided for the treatment of hypreproliferative diseases, such as cancer, using real-time computer control to visualize, to position and to operate drug infusing and imaging devices within the body of the patient. The invention employs a computerized imaging system (such as CAT scan, MRI imaging, ultrasound imaging, infrared, X-ray, UV/visible light fluorescence, Raman spectroscopy, single photon emission computed tomography or microwave imaging) to sense the position of a drug infusing catheter within the body. In a preferred embodiment, the invention provides real-time computer control to maintain and adjust the position of an infusion catheter and/or the position of the patient relative to the infusion catheter; and also provides real-time computer control of the operation of the infusion catheter based on images and/or computer models of the dispersion of one or more cytotoxic or other drugs or therapeutically active agents through the vascular bed of the neoplastic tissue being treated. In other preferred embodiments of the invention, vasoconstrictive drugs are applied locally based on computer modeling of blood flow patterns in order to channel blood flow carrying the cytotoxic drug or other therapeutic agent into the neoplastic tissue, and to minimize exposure of healthy tissue to such drugs.

17 Claims, 3 Drawing Sheets

OTHER PUBLICATIONS

Vokes, Everett E., and Samuel Hellman. "Advancing Current Treatments for Cancer," Scientific American: Sep. 1996, pp. 118–123.

Pelizarri, Charles A., and Maryellen L. Giger. "Advances In Tumor Imaging," Scientific American: Sep. 1996, pp. 110–112.

Old, Lloyd J. "Immunotherapy for Cancer," Scientific American: Sep. 1996, pp. 136–143.

Oliff, Allen, and Jackson B. Gibbs. "New Molecular Targets for Cancer Therapy," Scientific American: Sep. 1996, pp. 144–149.

Folkman, Judah. "Fighting Cancer by Attacking Its Blood Supply," Scientific American; Sep. 1996, pp. 150–154.

Gupta, Jyothi, and Li–Ping Han. "Development of Retinoblastoma in the Absence of Telomerase Activity", J. National Cancer Inst.: Aug. 1996; 88 1152–1157.

Morin, Gregg B. "Telomere Integrity and Activity," J. National Cancer Inst.: Aug. 1996; 88: 1095–1096.

Nelson, Nancy J. "Researchers Debate Clinical Role of Telomerase," J. National Cancer Inst.: Aug. 1996; 88: 1021–1023.

Ghil Chik, K. Mobel M. "Telomerase Activity in Human Breast Tumors," J. National Cancer Inst.: Jun. 1996; 88:839–840.

Schofield, Julie Anne, "Fiber Optics Quickly Detect Cervical Malignancies," Design News: Jun. 10, 1996; 62–64.

Gottsehalk, Mark A. "Fluorescence Spots Lung Cancer Earlier," Design News: Jun. 10, 1996; 66–68.

Hiyama, Eiso, and Lauren Gollahon. "Telomerase Activity in Human Breast Tumors," J. National Cancer Inst.: Jan. 1996; 88:116–122.

Rhyu, Michelle S. "Telomeres, Telomerase, and Immortality," J. National Cancer Inst.:Jun. 1995; 87:884–894.

Morin, Gregg B. "Is TelomeraseaA Universal Cancer Target?", J. National Cancer Inst.:Jun. 1995; 87:859–861.

Hiyama,Keiko, and Eiso Hiyama. "Telomerase Activity in Small–Cell and Non–Small–Cell Lung Cancers," J. National Cancer Inst.:Jun. 1995;87:895–902.

McCann, Jean. "Chromosome Ends Produce a Potential Means of Treatment," J. National Cancer Inst.:May 1995; 87:638–639.

SYSTEM AND METHOD FOR TREATING CELLULAR DISORDERS IN A LIVING BEING

BACKGROUND OF THE INVENTION

1. Field of the Invention

This invention relates to systems, methods and devices for the treatment of cellular disorders, such as cancer and other hypreproliferative diseases in select tissue in living beings (humans or animals) using real-time scanning, computer analysis and control to visualize, to position and to operate surgical, drug dispensing and imaging devices within the body of the patient. The invention employs a computerized imaging system (such as CAT scan, MRI imaging, ultrasound imaging, infrared, X-ray, UV/visible light fluorescence, Raman spectroscopy, single photon emission computed tomography or microwave imaging) or a combination thereof, to sense the position of diseased tissue within the body of a patient. In a preferred embodiment, the invention provides real-time computer control to maintain and adjust the position of an infusion device, such as a catheter and/or the position of the patient relative to the infusion catheter; and, in one form, also provides real-time computer control of the operation of the infusion catheter based on computer analysis of scanning signals defining images and/or computer models of the dispersion of one or more cytotoxic or other drugs or therapeutically active agents through the vascular bed of the neoplastic tissue being treated. In preferred embodiments of the invention, vasoconstrictive drugs are applied locally based on computer modeling of blood flow patterns in order to channel blood flow carrying the cytotoxic drug or other therapeutic agent into the neoplastic tissue, so as to minimize exposure of healthy tissue to such drugs.

2. Background of the Invention

Chemotherapeutic techniques for the treatment of cancer and other hyperproliferative diseases involving abnormal solid cellular growths using cytotoxic agents have been limited in their effectiveness by difficulties in delivering the agents to the affected tissue; maintaining a therapeutically useful concentration in such tissue and limiting the dispersion of the cytotoxic agent into surrounding, healthy tissue. This problem is especially acute where the cytotoxic agent is one which interferes with cell replication, since certain organs (such as bone marrow) cannot function properly without the rapid proliferation of stem cells. The immune system may be compromised by excessive use (or more precisely, excessive dispersion) of many otherwise-effective cytotoxic agents.

In U.S. Pat. No. 4,978,332 (Luck, et al.), the investigators suggest administering a cytotoxic agent in combination with a vasoconstrictive drug, on the theory that the vasoconstrictive drug will inhibit migration of the cytotoxic drug away from the site of application, which is said to increase its effectiveness.

My co-pending application Ser. No. 08/743,794, filed Nov. 5, 1996, entitled "System and Method For Treating Select Tissue In A Living Being," the disclosure of which is incorporated by reference herein, describes a variety of steerable catheters that can be positioned under computer control near or inside a tumor or other select area of tissue. (It will be understood that, although the word "tumor" is used generally herein, the techniques and systems described are applicable to a variety of neoplastic growths including but not limited to cancer, oncogenically transformed cells, carcinomas, melanomas, lymphomas, myelomas, both benign and malignant tumors, and sarcomas of defined or undefined or irregular shape.) By imaging both the select tissue area of interest within the patient and the location of the catheter itself, real-time adjustments can be made by hand or under computer control in the catheter position to attain and maintain it at a predetermined location relative to a select area within the patient's body, thus facilitating more-precise drug delivery as well as operations, such as laser surgery, on select areas of tissue.

Despite the described and other advances, application of cytotoxic agents and other drugs to tumors or other-diseased areas within the body has not achieved the level of precision needed to use potentially toxic drugs having low therapeutic ratios, with safety. Even if the drug is administered close to the diseased tissue, it may be (and usually is) carried elsewhere by blood circulation before it has had the desired effect at the point of introduction, and in concentrations high enough to do damage elsewhere in the body. There is a need for a system and method for controllably delivering cytotoxic drugs directly to target tissue; and subsequently controlling the diffusion of such drugs so as to maximize their contact (both from a concentration and time standpoint) with the diseased tissue being treated and to minimize contact with healthy tissue elsewhere in the body.

SUMMARY OF THE INVENTION

Figure 1:
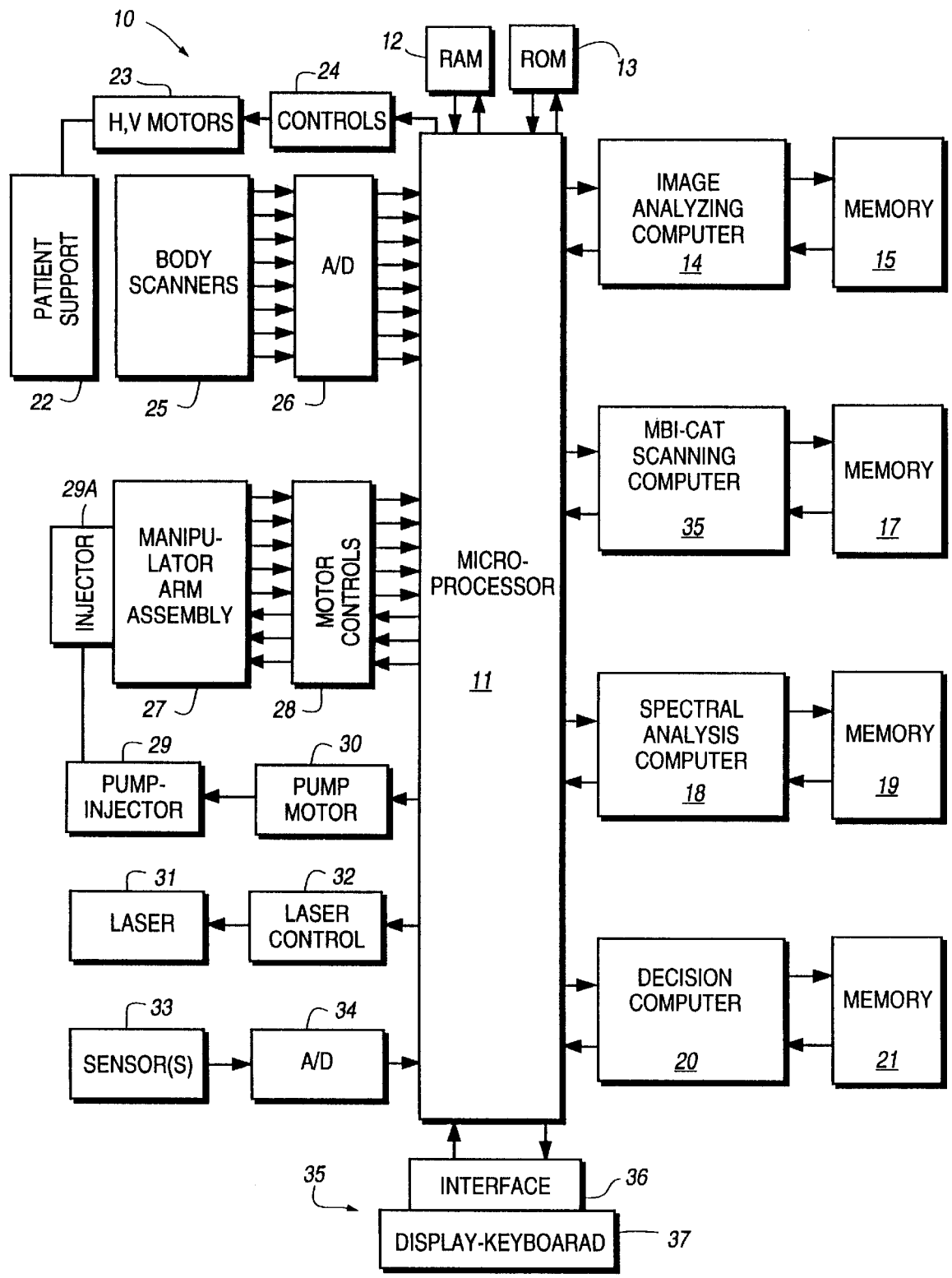
FIG. 1 shows one type of computer control system suitable for the real-time positioning of an endoscopic treatment and/or diagnosis system (such as a catheter suitable for practicing the present invention) within the body.

My invention provides a system and method for real-time, interactive computer control of the delivery and diffusion of cytotoxic drugs to select neoplastic tissue within the body, while limiting the unwanted dispersion of such drugs into adjacent, healthy tissue. This is accomplished by combining novel catheter positioning techniques with advanced imaging systems suitable for indicating the extent and boundaries of abnormal tissue areas; tracking the dispersion of tagged cytotoxic drugs or other therapeutically active agents through the vascular beds of such abnormal tissue; controlling dispersion by means of localized application of vasoconstrictive and, if desired, vasodilative drugs; and (in some embodiments) the selective withdrawal of blood containing high concentrations of cytotoxic drug or other therapeutically active agent downstream of the area of the diseased or abnormal tissue. In still other embodiments, the application of cytotoxic agents or other therapeutically active agents may be preceded, accompanied or followed by the localized alteration of blood flow patterns accomplished by the laser cauterization of select blood vessels to further limit and control the spread of the cytotoxic agents.

Therefore, it is a primary object of this invention to provide a system and method for effecting the precise, real-time computer control of the point or points of drug delivery within the body of a patient.

It is a further object of this invention to provide an imaging system and method that reveals diffusion of cytotoxic drugs throughout an area of diseased or abnormal tissue.

It is still another object of this invention to provide a method of delivering cytotoxic drugs, and controlling their diffusion within the body, by manipulating local blood flow patterns through the point injection of vasoconstricting and/or vasodilating drugs.

It is a further object of this invention to provide a method for predicting the extent and rate of diffusion of cytotoxic drugs within select diseased or abnormal tissues within the body, to enable the optimization of a drug treatment regimen to maximize exposure of diseased or abnormal tissue to such drugs while minimizing diffusion of such drugs elsewhere in the body.

It is another object of this invention to provide a system that can continuously or intermittently diffuse cytotoxic drugs into select diseased or abnormal tissue areas within the body, while continuously or intermittently withdrawing an unused cytotoxic drug before it can reach other parts of the body.

It is a further object of this invention to provide a system that can control diffusion of cytotoxic drugs by laser cauterization of select blood vessels before, during or after delivery of such drugs.

It is still another object of this invention to provide a system and method for diffusing monoclonal antibodies specifically to areas on and adjacent to tumors for use in immunodiagnosis and in therapy.

It is yet another object of this invention to provide a system and method that can diffuse radiosensitizers or other drugs in a controlled fashion in select tissue areas to render such areas more receptive to radiation treatment.

It is a further object of this invention to provide a method of precise, real-time computer control of drug delivery to select diseased or abnormal tissue within the body, preferably using a feedforward backpropogation neural network or a Hopfield neural network, capable of unsupervised learning, to observe the location of such diseased or abnormal tissue; to monitor the pattern of drug diffusion within such tissue and to control one or more parameters of such drug diffusion (such as the position of the introducing catheter; the amount of dilation of local blood vessels, the rate of drug introduction and/or withdrawal, etc.) so as to maximize exposure of the select diseased or abnormal tissue and to minimize diffusion of the drug to surrounding, healthy tissue.

These and other features, objects and advantages of my invention will be apparent upon consideration of the following detailed description of my invention.

DETAILED DESCRIPTION OF THE PREFERRED EMBODIMENTS

Computer Positioning Control

The present invention can employ imaging and computerized image analysis techniques based on sensors located external of the body (such as X-rays or Magnetic Resonance Imaging (MRI) sensors); images and coded image information derived from visual electrooptical sensors placed inside the body through a lumen of a catheter, or a combination of both types or still other of sensing systems or techniques. A variety of computer control systems can be used; one example appears in FIGS. 1 through 3.

The present invention will be described in terms of controlling a catheter, but it will be understood by those of ordinary skill that other types of drug delivery systems for insertion into the body of a patient also can be used.

In general, the location coordinates of select tissue of a living being in which a catheter-based operation is to be performed, are defined or computed with respect to images of the patient's anatomy showing anatomical structures which may be generated, for example, by employing computerized axial tomography (CAT scanning), magnetic resonance imaging (MRI), ultrasonography, positron emission tomography (PET), single-photon emission computed tomography (SPECT), infrared, X-ray or microwave imaging, or other types of electronic scanning by sensors placed outside the body. In accordance with the present invention, a computed image of a select anatomical area is generated by using one or more of the conventional imaging modalities mentioned above, and location coordinates with respect to a patient support structure are assigned to each pixel making up the image. The anatomical region into which it is desired to perform a catheter-based operation, such as the controlled injection of a drug, is then located on the electronically generated image or images by a radiologist, for example, with selected of the pixels making up the image of the region serving to define the injection or transplant location. A preferred means by which this can be performed is to display both the images of the catheter and the select anatomical region of the body on a display monitor having a manually positionable cursor for outlining an area containing the desired anatomical region. The operator of the system then inputs to a computers digital data in the form of codes defining the anatomical location at which an operation is to be performed, as represented by the select pixels within the outlined area. As described below, each pixel of the body or organ image displayed by the computer has assigned to it a set of location coordinates calculated or defined with respect to a support structure, such as a table supporting the patient while the imaging is performed (see FIGS. 2 and 3, discussed below). The same or a similar patient support structure is then utilized during the catheterization and drug infusion/withdrawal procedure. The catheter is moved manually or by a manipulator therefor under computer control, inserted into select tissue, and operated so as to perform the desired drug injection/withdrawal operation at select location coordinates with respect to the support structure.

Not shown, but assumed to form part of the computer 35 and its peripheral controllers ,are manual means for effecting selective operation of the described catheters, manipulators and the body tissue scanning devices, for use by medical personnel in supplementing the computer controlled operations in the performance of certain operations to detect and treat select tissue of the body. Computer controlled imaging, radar and laser range finding devices may also be employed to provide scanning signals for processing by an image analyzing computer 14, to permit the computer to further analyze the image content defined by select cross-sectional views or image slices generated by the CAT, PET, SPECT or MRI scanning system 25, so as to automatically determine the coordinates defining the depth, location and three dimensional shape of the transplant site or a growth or growths thereat and to provide coded control signals for effecting automatic surgery on select tissue or treatment, as described. Thus the body scanning system 25 may be employed by itself to generate computer analyzable image information or may be supplemented with image information generated by an electronic camera, such as a television camera and/or by one or more laser-photodetector scanning arrangements which are fixedly supported within the catheter or which show a view from the distal end of the catheter through a fiber optic bundle.

As noted above, feedforward backpropogation or Hopfield neural networks (or a combination thereof) can be employed from the beginning of a catheterization procedure to "learn" the proper location of the catheter with respect to adjacent tissues and to continuously maintain that position against changes in position and sensed appearance of the surrounding tissue that may be caused by patient respiration, movement, and by the catheterization and drug infusion/withdrawal procedures or variations in tissues structure or shape during the operation.

In the case of diseased tissue having such conditions as dysplasia or cancer, imaging and visualization of such tissue (by contrast with surrounding healthy tissue) also can be accomplished in a variety of ways. For example, tumor localizing drugs such as Hematoporphyrin derivatives or Porfimer sodium or Photofrin, which are preferentially absorbed by tumors and which fluoresce when exposed to certain wavelengths of light, can be used. It also has been observed that some tumors as well as precancerous lesions of lung or other tissue exhibit decreased overall fluorescence intensity in the green region of the visible spectrum, which may be due to a reduced level of oxidized form of riboflavin. See U.S. Pat. No. 5,507,287 (Palcic, et al.). Other tumors may show behavior in which the fluorescence spectra of cancerous tissues is different from normal tissues in that the maximal fluorescence peak of tumor tissues s blue shifted to lower wavelengths. See U.S. Pat. No. 4,930,516 (Alfano, et al.). These phenomena may be used as a basis for delineating the extent of diseased or abnormal tissue (cancer or dysplasia or metaplasia) by visual observation using a catheter of the type described in my co-pending application Ser. No. 08/743794, filed Nov. 5, 1996, referred to above.

Detection of fluorescence, in connection with the foregoing techniques, can be accomplished by observation using a steerable catheter having a collection lens system and a plurality of fiber optic light pipes or cables to transmit collected light to one or more external sensors or imaging devices. Alternatively, one or more miniaturized, image-intensified charge-coupled detectors (CCD's) or arrays thereof may be used in the catheter itself. Specificity to particular wavelengths of light for each CCD can be provided using filters or dichroic means. He/Cd laser light is one preferred light source for such work. In addition to the laser light images, white light (for example, from a Xenon incandescent bulb) may be provided, to create a color image of the target area onto which information derived from fluorescence may be superimposed)

Additional imaging techniques for delineating the extent of tumors or other neoplastic growths may include temperature measurement, it being noted that some neoplastic growths exhibit higher temperatures than surrounding tissue, partly as a result of having obtained a more generous blood supply. Imaging also may be accomplished by injecting a solution of monoclonal antibodies specific to the type of neoplastic cells being treated, conjugated to a radioactive imaging marker such as a radioisotope of Iodine, Indium, Tecnium or Gadolinium, which allows imaging using PET scanning or NMR scanning. See U.S. Pat. No. 5,500,346 (Bright, et al.); U.S. Pat. No. 5,512,443 (Schlom, et al.), the disclosures of which are incorporated by reference herein.

To facilitate use, crosshairs may be projected onto the screen and a mouse or other pointing device may be used to provide positioning instructions. When used with catheters containing fiber optic bundles, one or more strands of the bundle may be used to project a beam of laser light onto surrounding tissue for aiming purposes, while the remaining fibers are used to transmit images.

To facilitate pinpointing of the catheter position, a variety of devices may be used depending on the sensing modality. In the case of ultrasonic sensing, for example, a closed cavity in or near the distal end of the catheter (or at some other location along the length of the catheter that must be pinpointed with precision) will act as a resonator to make the location appear clearly on the ultrasonic image. In the case of X-ray or MRI sensing, metal foil inserts or electronic circuitry can serve the same function. Active RF antennas also can be included at the desired point(s) inside the catheter.

In one embodiment, the patient is required to be in the same position with respect to the support structure during both the imaging and catheterization and drug injection/withdrawal procedures, so that the location coordinates selected will correspond to the proper anatomical region of the patient. One way of accomplishing this is to use a patient support structure having a moldable support structure defining a surface that can be made to conform to the shape of the patient's body as a kind of body cast. Once such a body impression is made, the patient may be placed in substantially the same position on the support structure for both scanning/imaging and subsequent surgical or transplantation procedures. Such a moldable patient support may also serve to immobilize the patient during both procedures. Other patient restraint devices, such as straps and adjustably positionable table stops, may also be employed.

The manner of assigning location coordinates to each image pixel depends on the particular imaging modality. For example, with a conventional CAT scanner, the x-ray source or tube emits a narrow beam of x-rays toward the patient with an x-ray detector, such as an array of scintillation detectors, positioned on the opposite side of the patient on which an x-ray shadow is formed. The x-ray generator and detectors, mounted on a rigid gantry, are rotated in multiple steps about the body until an entire axial slice is viewed from multiple angles. Codes defining the data acquired by the scintillation detectors are entered into a computer which uses mathematical algorithms to reconstruct a cross-sectional image or images of slices of the region examined. Such a computerized scanning arrangement calculates the degree to which the tissue interposed between the x-ray tube and the detectors absorb the x-ray beam and thereby provides an attenuation coefficient for each area of tissue examined. Essentially, the quantity of x-rays absorbed in small volumes (voxels) of body tissue in each slice is computed. Computer analysis of the image signals and data collected then allows assignment of a numerical value to each small area (pixel) of the cross-sectional plane. By means of a digital-to-analog converter, the numerical value of each pixel is translated to a gray or color scale for driving a CRT display or the like and may be employed for automatic control.

Due to the nature of the CAT scanning image reconstruction algorithm, the computer necessarily must assign location coordinates to each pixel with respect to the x-ray detector in order to generate the displayed image. Such coordinates are computed with respect to the patient support structure in the axial plane which is being imaged. In order for such coordinates to be useable for properly directing a transplantation or other tool in accordance with the present invention, however, they must be scaled and combined with another coordinate along the axial axis. In order to assign an axial location coordinate with respect to the patient support structure for each pixel, the positions of the x-ray tube and detector with respect to the patient support surface are sensed, and digital signals are generated that are input to the computer during the imaging procedure. The location coordinates for each pixel making up the image with respect to the patient support structure may be then readily calculated.

In pulse-echo ultrasound techniques, an ultrasonic pulse is transmitted through the body tissues with the reflected echoes from each acoustical interface is sensed by a transducer and the signals are computer processed in order to provide a train of digital signals that define an image of the underlying structure. In so-called B-mode ultrasound, the pulse-echo procedure is performed in scanning matter to provide signals for imaging the underlying morphologic structures in a tomographic format. The resulting scanning signals, after digitization, are used by an electronic computer to construct a two-dimensional array of pixel values for driving a display. In order to construct an image, each pixel is assigned a coordinate location with respect to the transducer in the same plane along which the ultrasound is transmitted. Conventional ultrasonic scanning, however, requires that the ultrasonic transducer be contacted or coupled to the body surface or tissue over the region to be examined and positioned so as to scan at various angles. In order for the computer to compute the location coordinates for each pixel making up a display of an ultrasonic scan, the transducer is mounted on a movable arm assembly or robot having sensors in its joints for producing signals proportional to the degree of flexion or rotation of each such joint, which sensors generate signals that are then fed to the computer for calculating the arm's position and orientation. Using appropriate scaling factors, the location coordinates for each pixel making up the image with respect to the patient support means may be readily calculated by a computer processing the abovementioned data.

Computerized image construction in conventional MRI scanners, for employment in the present invention, is similar to that used in CAT scanners in that intensity values for an array of pixel values are computed with each pixel value which is stored in the computer being assigned a set of location coordinates in order to generate the reconstructed image. In MRI scanning, nuclei such as protons are subjected to a magnetic field gradient, referred to as the slice-select gradient, which varies along the axis perpendicular to the plane of the image. Certain protons (such as hydrogen nuclei of water molecules in the tissue being scanned) within the magnetic field gradient are excited to resonance by a so-called 90 degree RF pulse which causes them to emit detectable radiation. The amplitude and frequency of such emitted radiation is used to assign proton density values to pixels and generate the MRI image. The location coordinates of each pixel in the image are calculated with respect to the patient support structure within the plane of the image cross-section, assuming the receiver coil of the MRI scanner remains at a fixed distance from the patient support structure. In a modified form, such location coordinates may be calculated with respect to base lines or select points at select locations of the image(s) generated, such as the intersection of blood vessels with an organ or a tumor, a select portion of an organ, etc. In order to derive an axial coordinate value (i.e., along an axis perpendicular to the plane of the cross-sectional image) for each pixel, it is necessary for the computer to compute the distance along the slice-select gradient with respect to the patient support structure or the base line or points established, where the Larmor frequency of the excited nuclei corresponds to the frequency of the 90 degree RF pulse. Such a computation only requires that the computer be supplied with data reflecting the magnitude of the slice-select gradient field versus distance and the frequency of the RF pulse which can either be assumed to be in accordance with computer command or can be sensed by magnetometers and a separate RF receiver coil. MRI scanners also allow the particular gradient fields to be generated along arbitrarily chosen axes so as to produce images not only in the transverse plane but also in coronal, sagittal, and oblique planes. The axial coordinate for each image is then computed in the same way as just described, but the coordinate is then along an axis perpendicular to the plane of the cross-sectional image. Finally, since the patient support structure and the MRI imaging apparatus are relatively moveable with respect to one another, the computer is fed with data produced by position sensing means so that the location coordinates can be translated so as to be with respect to the patient support structure.

Once the location coordinates defining the select body region at which it is desired to perform the catheterization or drug infusion/withdrawal operation have been calculated by the computer, the catheter is inserted (either manually by surgical personnel or under computer control by one or more robots or manipulators) and the catheterization operation (for example, select drug injection and/or withdrawal) is performed. The process may then be repeated at different sites in the select body region. As will be described more fully below, electro-optical sensing and monitoring means may be provided, allowing the effects of the catheter operation to be monitored by the computer and the results of such monitoring may be used to control further injections.

FIG. 1 shows a computer system 10 for effecting the automated performance of a catheterization and drug infusion/withdrawal procedure in accordance with the invention. The catheter may be automatically positioned with respect to the patient by means of a multiple axis electromechanical manipulator the motors of which are controlled in their operation by coded control signals generated as a result of scanning that portion of the patient's body where it is desired to effect the particular catheter operation such as angioplasty, drug delivery or other operations. A catheter may be similarly directed under computer-control to an intraductal or other internal body site. Alternately, the catheter may be introduced manually using any of a number of known techniques including Seldinger insertion or the use of a split-sheath introducer, with the aid of control signals generated by the computer analysis of a real-time computer image of the location and path of the catheter, or its operating end or head.

The scanning signals may be generated by one or more known scanning devices, such as a nuclear magnetic resonance (NMR or MRI) scanning system, a computerized axial tomography (CAT) scanning system employing x-ray scanning, a PET scanning system, a SPECT system; thermographic techniques; various infrared or spectrographic scanning systems operable to generate image signals of tissue and bones, or ultrasonic pulse-echo scanning systems. Such scanning signals may be computer processed and analyzed to generate multiple cross-sectional views, such as parallel slice images of the portion of the body, where it is desired to operate. The image information defined in the cross-sectional views or slices of the body tissue may be digitized to generate trains of digital (picture) signals which are analyzed by a computer wherein resulting code signals are generated defining the borders of the anatomical structures and which may be further computer processed to provide further code signals indicative of coordinate locations of those structures. Such coded information may be used by the computer to control the operation of an automatic multi-axis manipulator for a catheter device, such as a heated or cryogenically cooled scalpel, a hollow needle or ablation device, a rotary cutting tool, a combination thereof, etc., to automatically position and insert the catheter, guide it to pass through intervening tissue or body ducts to reach the specific location where the catheterization operation is to be performed. Alternatively, the computer control system may simply be used to observe the manually-controlled passage of the catheter to the desired location, using the scanning system.

In one form of operation, raster or other scanning of tissue of a living being containing a defined (or undefined) tumor( ) with a radiation beam such as a selectively tuned laster beam (and/or an actual or reconstructed image of images thereof (generated, for example by CAT, MRI, PET, SPECT or other form of penetrating radiation scanning), and the computer analysis of the resulting image and/or spectral (fluorescence) scanning signals, results in the generation of (coded) coordinate signals which define the border(s) or outer surface of the detected tumor. In other words, as the scanning beam(s) crosses the border between normal and cancerous tissue, detectable variations occur in either or both the image and spectral (fluorescence) signals, which variations define the outer limits or border of the cancer or tumor. The resulting border or location defining code signals are then employed intelligibly indicate and to guide the physician in creating an optimum drug infusion/withdrawal treatment regimen.

Where the tumor being treated is not well defined, code signals generated as described above may be indicative of the shape or contour of a thin layer of generally normal tissue, such as a shell-like envelope or layer thereof surrounding the tumor of such shape and of sufficient thickness to account for any extensions, such as dendrites or other fine extensions of the tumor or malignancy or other cancerous cells therefrom. In other words, the shape and thickness of such outer layer is such as to provide the patient with malignant-cell-free tissue remaining after the operation.

The coordinate location indicating and surface defining code signals are generated by the automatic computerized analysis of either or both image and spectral signals generated when the tumor and adjacent normal tissue are scanned with radiation, such as one or more raster scanned laser beams and/or other forms of radiation such as employed in CAT, MRI, PET, SPECT, thermographic, infrared, ultrasonic microwave, tera hertz or other forms of computerized tissue scanning. Laser beams generated at select frequency or wavelength may be employed to self-excite cancerous and/or precancerous tissue to emit select spectral fluorescence radiation which may be detected and discriminated from fluorescence radiation, if any, generated when adjacent non-cancerous radiation is so eradicated. Using CIA (computerized image analysis), the extremities or surface shape of the tumor may be defined in terms of surface coordinate indicating code signals which may be employed to control a drug injection/withdrawal procedure or a radiation-surgical procedure.

For tumors of well-defined shape, the computerized image analysis of reflected and/or penetrating radiation intersecting the tumor and adjacent tissue will permit the computer to calculate code signals which are indicative of the shape of the tumor.

Such scanning is effected under computer control and also surgically operates on (the shell shaped) tissue adjacent the tumor detected or computed to possibly include free cancer cells from the tumor, dendrites or fine extensions of the tumor and/or the paths of blood vessels leading to and feeding the tumor.

Advantageously, a control algorithm utilizing a layered feedforward backpropogation neural network or a Hopfield neural network (or a combination of both) may be used. A Hopfield network, which can be arranged so as to be able to compare the pattern of approach to the desired location chosen by the surgeon and thereby "learn" the pattern of movement required to maintain the desired location against changes in position of the catheter or the patient caused by breathing, muscle expansion or contraction, etc. By minimizing the Hamming distance between the actual location at a given time and the "learned" location set by the surgeon during introduction of the catheter, the computer control system can effectively maintain the catheter position despite ongoing changes in the image of the location caused by physiological changes in the patient's tissue during the catheterization, imaging operation or drug infusion/withdrawal procedure.

Figure 2:
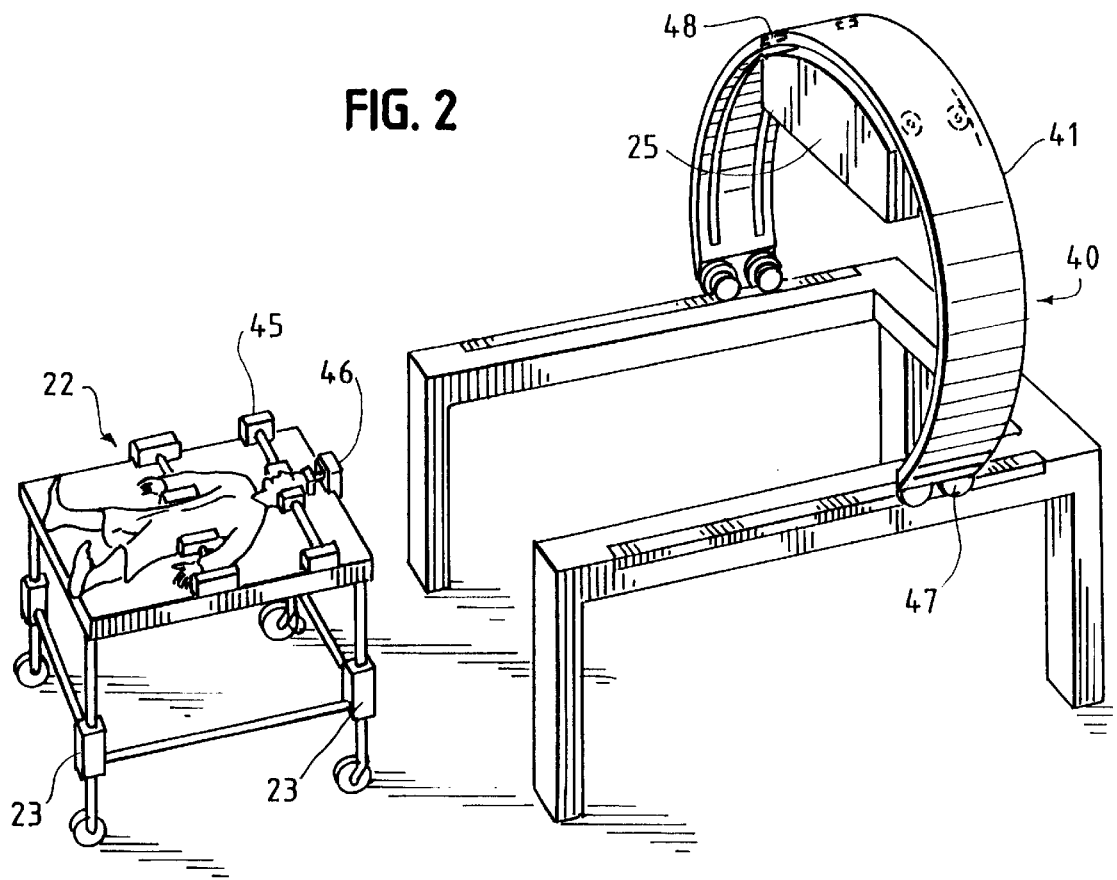
FIG. 2 shows a patient orientation system which optionally can be used to help control the position of the endoscopic device or catheter within the body.
Figure 3:
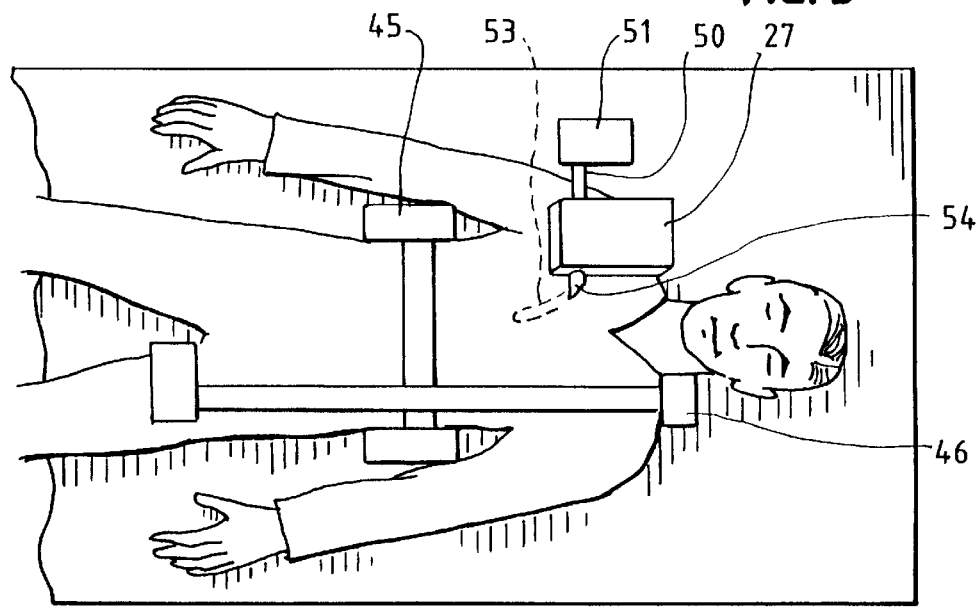
FIG. 3 shows further details of a patient orientation system which optionally can be used to help control the position of the endoscopic device or catheter within the body.

System 10 includes a number of computers, devices and subsystems which are automatically controlled in their operation or generate feedback information in the form of signals passed through a control computer or microprocessor 11. (Preferably, such feedback information is processed using an appropriate backpropagation function and presented to the output layer and/or the hidden layers of a neural network used to control catheter position.) An image analyzing computer 14 with an attendant programmable memory 15 analyzes image information generated by an NMR or CAT scanning computer 16 with attendant memory 17 which receives digitized image information from a plurality of MRI sensors 25, which can scan or sense a select portion of the body of a patient held immovable against a patient support or table 22, which is motorized and driven in multi-axis movement by a plurality of gear motors 23 (see FIG. 2), the controls 24 of which are operated by trains of digital control signals passed through microprocessor 11 from either manual controls and/or one of the computers connected to the microprocessor. In addition, patient positioning motor operated assemblies 45 and 46 may be directly coupled to specific portions of the patient's body as shown in FIGS. 2 and 3, allowing particular parts of the patient to be motor driven and moved relative to the patient support 22 to further provide fine positioning of the patient relative to the sensor and catheter. Again, one or more neural networks designed for unsupervised training may be used to evaluate and weight the effects of moving the patient support 22 in comparison with the effects of moving the patient himself using motor operated assemblies 45 and 46. With this approach, the computer progressively learns how best to maintain catheter position during the procedure by altering the weights used at each layer of the neural network as the catheterization procedure progresses.

Conventional CAT and MRI scanning arrangements generally rotate and axially move the patient through the scanning field. In addition, the MRI, CAT, or PET body scanners or array of sensors 25 may also be supported on a mount 41 which is driven by motors 47 and 48 and controlled to move about and/or along one or more axes by means of a computer, such as a decision computer 21, connected to the microprocessor and operable to analyze the signals output by one or more of the computers 14 and 16 to effect proper control of the treatment operation and/or at least a portion of the scanning operation. The analog image signals output by the body scanners are converted to trains of digital image signals by one or more analog-to-digital converters 26 which pass such trains of signals through microprocessor 11 to the MRI or CAT scanning computer 16 for analysis and conversion to useable image information for analysis by the image analyzing computer 14.

In the preferred embodiment, a catheter positioning manipulator 27 is supported adjacent the patient support 22 to which it is preferably connected. The catheter positioning controller/manipulator 27 is driven by a plurality of gear motors or hydraulic or electromechanical positioners (not shown) which are used to manipulate the proximal end 50 of the catheter outside the insertion point 54, thereby affecting the location of the distal end 53 of the catheter. Such manipulation of the catheter may include simply movement of the proximal end of the catheter. It may also include manipulation of the catheter shape within the body using various types of steering mechanisms.

As in the case of the patient positioning devices, one or more neural networks designed for unsupervised training may be used to evaluate and weight the effects of moving the patient support 22 in comparison with the effects of moving the proximal end of the catheter; manipulating the steering mechanism (if any) by using catheter steering controller 51; and moving the patient himself using patient positioning motor assemblies 45 and 46. With this approach, the computer progressively learns how best to maintain catheter position during the procedure by altering the weights used at each layer of the neural network as the catheterization procedure progresses.

The control signals generated thereby are sent to a bank of controls 28 which receive and pass direct command control signals from the computer 20 and apply feedback signals from the various manipulator motors to effect a suitable degree of precision operation of the catheter while its operating head is in alignment with select tissue to be treated or operated upon thereby.

A sensor or sensor array 33 may be located in the catheter at or adjacent its distal end 53 and may be operable to receive light reflected from tissue adjacent the end of the catheter. An optical fiber light pipe may extend from the output of the laser 31 through and to the open end of the catheter to conduct laser light to tissue adjacent the open end of the catheter while a second optical fiber may extend from such open end, back up the catheter or along another light pipe in the catheter to the sensor 33. Resulting spectral radiation emitted by the tissue intersected by the laser radiation is passed to the end of the optical fiber adapted to receive same and back along such fiber to the photodetector at the other end thereof which generates an analog electrical signal modulated with spectral information relating to the tissue intersected by the laser light. Spectral information such as Raman spectra can be used to analyze and detect or diagnose the tissue scanned and to distinguish plaque deposits from healthy tissue at the walls of blood vessels, for example. Cancerous and precancerous cells and tissue may be thus detected and discriminated from normal tissue by computer analysis of such spectral radiation signals.

Also shown connected to the control computer or microprocessor 11 via an interface 36, is a computer 35 such as a workstation or PC, which includes a display and a keyboard which is operable to input data to a random access memory or RAM 12 or any of the computers 14, 16, and 18 or to control the operation of the manipulator 27, pump motor 38 and laser 31 or a plurality of such subsystems and devices for performing the described treatment or surgical operations. It is noted that the pump 29 may be varied in its operation in accordance with the control signals generated by the decision computer 20 and applied to a controller for the pump-motor to predetermine the quantity and rate of flow of drugs pumped to or withdrawn from the injector 29A after its injection tube or tubular needle has been driven under computer control to a select location with respect to select tissue. A plurality of pumps, such as pump 29, may be operated by respective pump motors and may be provided mounted on the operating head of the manipulator, each of which pumps is operable to force flow a different medical material from a respective of a number of reservoirs to the needle or tube of the injector 29A or to separate injectors therefor. Peristaltic pumps that use rollers to compress short lengths of replaceable plastic tubing may be especially suitable for this purpose.

When drugs are being withdrawn from a select portion of a patient's body, as described below, the catheter advantageously may be inserted into a blood vessel using known techniques and may include therein or in the injection needle means for measuring blood pressure (such as a pressure transducer) and/or flow rate (such as a mass flow meter or hot wire). Blood pressure and flow information can be used as described below in monitoring and controlling drug dispersion.

Controlled Infusion And Withdrawal Of Cytotoxic Drugs

Figure 4:
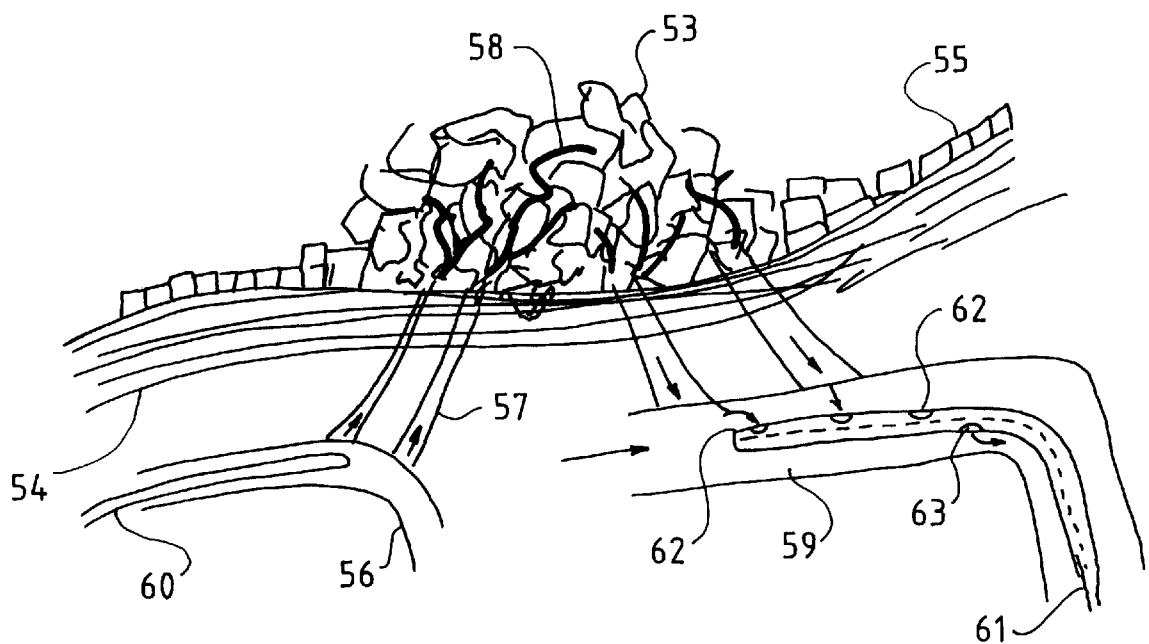
FIG. 4 illustrates how the progression of a tagged cytotoxic drug can be monitored through a tumor and its diffusion controlled using the present invention.

The system described above may be used advantageously to administer controlled doses of cytotoxic or genetic drugs useful in the treatment of various forms of cancer and other hyperproliferative diseases. FIG. 4 illustrates one system that can be used in the preferred procedure described below.

Schematically illustrated is a primary tumor 53 which has begun to grow on a basement membrane 54, surrounded by normal epithelial cells 55. The tumor has established a rich blood supply from artery 56, through arterioles 57 and into capillaries 58 within the tumor 53. Blood flows out of the tumor 53 and into vein 59.

In a preferred embodiment of the method of this invention, the extent of the tumor 53 is first determined by one or more of the scanning techniques described above. For example, a first or infusion catheter 60 may be advanced through artery 56 to a position near the tumor and a solution of monoclonal antibodies specific to the type of neoplastic cells being treated, conjugated to a radioactive imaging marker such as a radioisotope of Iodine, Indium, Tecnium or Gadolinium may be infused into the artery. The location of the infusion catheter 60 may be monitored and controlled using the computer control techniques described above. The monoclonal antibodies, together with the imaging marker, attach preferentially to the neoplastic cells of the tumor 53, which allows imaging of the extent and boundaries of the tumor using PET, CAT, or NMR scanning.

In an optional next step, an angiographic contrast medium, such as a radioactive marker differing from the imaging marker used initially, is injected through the infusion catheter 60 and is allowed to flow through capillaries 58 to provide imaging of the pattern of blood flow into and out of the tumor 53. That image may be superimposed on the image of the tumor created using the technique described above, to provide data concerning both the extent of the tumor and also the pattern of blood flow through it. Blood pressure and flow rate data also can be collected through instrumentation in the infusion catheter 60 at the same time. Such data can be used to calculate, among other parameters, the uptake and clearance volumes and time constants for the affected tissue.

In another approach to blood flow modeling, a second (withdrawal) catheter 61 may be positioned in a vein downstream of the tumor. Nitrous oxide; hydrogen and/or labeled radioactive Krypton gas isotope pulses may be injected through infusion catheter 60 and venous blood continuously sampled through withdrawal catheter 61. The resulting concentration vs. time data can be used to calculate overall uptake and clearance volumes and time constants for the tumor tissue. See, for example, Stanley Middleman, *Transport Phenomena in the Cardiovascular System*, at 181 (1972).

It will be understood that approaches may have to be made to more than one artery and/or more than one vein, and multiple mappings may have to be accomplished to fully define the vascular bed of the tumor in some instances.

In still another optional step, blood samples obtained from withdrawal catheter 61 may be analyzed in vitro using known techniques such as sandwich immunoradiometric assays (IRMA) to detect the extent, if any, to which metastasis is occurring as neoplastic cells may be migrating into the venous blood leaving the primary tumor site.

Samples of blood obtained from withdrawal catheter 61 also may be used (particularly where metastasis is occurring) for extracorporeal assays such as autoradiographic detection of telomerase and measurement of telomere length to monitor the success of the treatment. See, for example, U.S. Pat. No. 5,489,508 (West, et al.).

Given the data thus accumulated concerning the location of blood vessels supplying the tumor, the extent (volume and area) of the tumor and the pattern of blood supply, the optimum dose of cytotoxic drug can be calculated using known fluid mechanical modeling techniques, such as potential flow modeling, or distributed parameter modeling Runge-Kutta simulation to model the dispersion of various concentration/time dose patterns of drug through the tumor, combined with clinical data relating to the response of the particular type of tumor to the chosen cytotoxic drug. Among the cytotoxic drugs that can be employed therapeutically using the system and method of this invention are alkylating agents, enzyme inhibitors, proliferation inhibitors, lytic agents, DNA synthesis inhibitors, membrane permeability modifiers, DNA intercalators, antimetabolites, or the like. Illustrative drugs include: cisplatin (Platinol), doxorubicin hydrochloride (Adriamycin), bleomycin sulfate (Blenoxane), fluorouracil, vincristine sulfate (Oncovin), vinblastine sulfate (Velban) VP-16, chlorambucil (Leukeran), melphalan (Alkeran), busulfan (Myleran), carmustine [BCNU] (BiCNU), lomustine [CCNU] (CeeNU), streptozotocin, thiotepa, dacarbazine (DTICDOME), methotrexate, cytarabine (Cytosar-U), azaribine, mercaptopurine (Purinethol), thioguanine, actinomycin D, plicamycin (Mithracin), mitomycin-C (Mutamycin), asparaginase MSD (Elspar), procarbazine hydrochloride (Matulane), prednisone, prednisilone, triamcinolone, testosterone, estrogen, insulins, and hydroxyurea (Hydrea). Other drugs of interest include radiosensitizers, such as SR-2508 and misonidazole: hyperthermia sensitizers, such as lidocaine and marcaine, bioreductive agents, such as mitomycin benzotriazine dioxides and nitroheterocyclic compounds such as benznidazole.

The dose (concentration and time) of the cytotoxic drug may be controlled in a number of ways. In some instances it may be sufficient to select, based upon the images created as described above, the optimum injection point to which to advance the infusion catheter 60, and to calculate the time period(s) of the dose(s) of cytotoxic drug to be administered. At an appropriate later time, another pulse of tagged monoclonal antibodies may be administered to observe the progress of treatment and to adjust the dosage, if required.

It will be apparent that more than one drug injection point may be used, depending upon the size of the tumor and the points of blood supply to its vascular bed. Similarly, if a withdrawal catheter is used as described below, there may be more than one withdrawal point.

In an optional, alternative approach, controlled doses of vasoactive drugs may be administered together with, or separately from, the therapeutically active cytotoxic drugs. For example, a third infusion catheter (or a distal port in infusion catheter 60) may be used to administer a vasoconstrictive drug into artery 56 downstream of the point of injection of the cytotoxic drug. Suitable vasoconstrictive drugs include sympathomimetics including the catecholamines, norepinephrine, epinephrine, isoproterenol, dopamine, and related compounds such as ephedrine and other phenylisopropylamines, phenylephrine, amphetamine, metraminol, methoxamine; ergot alkaloids including lysergic acid, lysergic acid diethylamine, ergonovine, methylergonavine, methysergide, ergotamine; the angiotensins; and the prostaglandins. By constricting the smooth muscle of the artery 56 downstream of the capillaries 58 that feed the tumor, a larger proportion of the cytotoxic drug can be directed to the tumor and the distribution of the drug elsewhere in the body can be limited.

A still further improvement on the dose control and limitation of dispersion can be achieved by advancing a withdrawal catheter 61 to an appropriate point in vein 59, and withdrawing from vein 59 blood that may be carrying a quantity of non-absorbed cytotoxic agent before it can reach other parts of the patient's body. In a preferred approach to that improvement, a dual lumen catheter may be used having one or more withdrawal openings 62 to withdraw blood from downstream of the vascular bed of the tumor. The dual lumen catheter has one or more injection openings 53, which are used to supply cleansed blood just downstream of the withdrawal openings. In this way, blood contaminated with cytotoxic drug can be removed before it circulates through the rest of the body, cleansed extracorporeally using a dialysis machine or artificial liver (not shown) and reinjected, which further limits undesired distribution of the cytotoxic drug to other parts of the body. It will be understood that contaminated blood also could be disposed of and replaced, if necessary, with blood stockpiled from earlier donations by the patient or from some other source.

In yet another embodiment of the invention, a vasoconstrictive drug may be administered to veins downstream of the tumor using a catheter advanced through such veins for that purpose. The cytotoxic drug may then be administered through infusion catheter 60. The restriction of blood flow through vein 59 acts to retain the cytotoxic drug in the tumor for a longer period of time, and at a higher concentration than would otherwise be achievable.

In a variation on this embodiment, after mapping of the vascular bed and surrounding arteries, laser cauterization can be employed to seal off selected arteries downstream of the arterioles and capillaries feeding the tumor, thus ensuring that essentially all of the cytotoxic drug, administered to the patient through infusion catheter 60, reaches the tumor.

In yet another embodiment of the preceding version of the invention, after administration of the vasoconstrictive agent to vein 59, infusion catheter 60 is used alternately to inject and withdraw blood or saline containing the cytotpxic agent, thereby maintaining a high concentration of cytotoxic agent within the tumor over a protracted period of time.

In a preferred addition to the foregoing embodiments, the cytotoxic drug itself may be conjugated to an imaging marker or simply mixed therewith. Preferably that marker should be distinguishable from the one used to map the vascular bed of the tumor. This will enable the physician operating the system to dynamically observe and control the distribution of the drug itself.

In still another preferred alternative embodiment, a feed-forward backpropogation neural network or a Hopfield neural network, capable of unsupervised learning, may be to observe the location of such diseased or abnormal tissue; to monitor the pattern of drug diffusion within such tissue and to control one or more parameters of such drug diffusion (such as the position of the introducing catheter; the amount of constriction of local blood vessels, the rate of cytotoxic drug introduction and/or withdrawal, etc.) so as to maximize exposure (time and concentration) of the tumor and minimize diffusion of the drug to surrounding, healthy tissue.

In still another addition to the foregoing embodiments, one or more sensitizing agents may be infused before or together with the cytotoxic drug. Such sensitizing agents include radioactive pellets, e.g., radionuclides such as technicium or iridium; radiation sensitizers, e.g., nitroimidazoles and halogenated pyrimidines (BUdR): repair inhibitors, e.g., methylated xanthines: bioreductive agents, which are activated only in hypoxic cells; cytokines, such as the interferons, lymphokines, such as interleukin-2; tumor growth inhibitors, such as tumor necrosis factor, transforming growth factor-beta, and the like.

Use Of Antiangiogenic Agents

Yet another addition to the foregoing embodiments involves the application of antiangiogenic agents to the vascular beds leading into and pervading the tumor. Such agents include proteins that interfere with alpha$_v$beta$_3$ integrin; angiostatin; and such drugs as CAI (which inhibits the influx of calcium into cells and suppresses proliferation of endothelial cells); CM101 (which destroys capillaries); interferon alpha (which decreases production of angiogenic proteins, thereby limiting capillary growth); interleukin-12 (which increases production of inducible protein 10, an angiogenic inhibitor); marimostat (which inhibits formation of enzymes useful in cell migration); pentosan polysulfate (which blocks action of growth factors in endothelial cells); platelet factor 4, TNP-470 and AGM-1470 (which inhibit proliferation of endothelial cells); and thalidomide. As disclosed above, such agents can be administered together with an angiographic contrast medium to enable observation of their distribution through the vascular bed of the tumor.

It is noted that in therapy with antiangiogenic agents, because of their toxicity to healthy tissue they are severely limited in usefulness. By initially mapping the vascular bed surrounding the tumor; dynamically sensing the distribution of the agents as they are applied and controlling their distribution through selective, computer-controlled local application of vasoconstrictive (or vasodilative) drugs, much higher dosage levels (time and concentration) can be achieved and sustained with minimum damage to surrounding healthy tissue.

Promotion of Radiation Therapy

In yet another embodiment of the present invention, instead of cytotoxic agents, the active drugs used may be radiosensitizers, such as SR-2508 and misonidazole; nitroimidazoles and halogenated pyrimidines (BUdR). Such agents may be infused using essentially the same procedures described above. In treatment using such agents, once the shape, size and boundaries of the tumor have been mapped and a satisfactory distribution of radiosensitizing agent has been achieved throughout the tumor (again, while limiting exposure of downstream healthy tissue using techniques disclosed above), one or more beams of tissue altering or destroying radiation (neutrons, protons, etc.) may be focused on the tumor to destroy the cells thereof. Adaptive computer control using a neural network approach may be used to optimize radiation dose to the tumor while minimizing exposure of surrounding healthy tissue.

In a preferred version of this embodiment of the invention, the location information gathered as described above is used to conform the shape, intensity and scanning of the radiation beam to the tumor volume, further minimizing exposure of healthy tissue.

In still another variation on this embodiment of the invention, the vascular map created as described above is used as a template to direct tissue destroying radiation (such as laser radiation) specifically at the arteries and/or arterioles supplying the tumor, thereby depriving it of its blood supply and causing destruction of at least a portion of the neoplastic cells. Such an operation advantageously can be combined with antiangiogenic agent therapy, as described above.

It will be apparent to those of ordinary skill in the art that many changes and modifications may be made while remaining within the scope of my invention. I intend to cover all such equivalent structures and methods, and to limit my invention only as specifically delineated in the following claims.

I claim as my invention:

1. A method for treating a tumor in a body which is in communication with arterial and venous blood flow comprising:
    a. mapping the surface and volume of said tumor;
    b. locating the arteries upstream of said tumor;
    c. calculating an optimum controlled dose of a cytotoxic drug suitable for treating said tumor;
    d. infusing a controlled dose of said cytotoxic drug into said tumor from one or more of said arteries at select locations upstream of said tumor; and
    e. withdrawing blood from one or more veins at select locations downstream of said tumor for extracorporeal treatment to remove said cytotoxic drug from the blood withdrawn whereby a substantial portion of said cytotoxic drug is infused into said tumor and prevented from diffusing into said body.

2. The method of claim 1, further comprising controlling the dispersion of said cytotoxic drug by injecting a vasoconstrictive drug into said arteries at select locations downstream of the select locations upstream for infusion of said cytotoxic drug of said cytotoxic drug.

3. The method of claim 1, further comprising locating the veins downstream of said tumor, and controlling the dispersion of said cytotoxic drug by injecting a vasoconstrictive drug at select locations into said veins.

4. The method of claim 3, further comprising alternately injecting and withdrawing fluid containing a cytotoxic agent at said select locations within said arteries.

5. The method of claim 1, further comprising injecting cleansed blood into said one or more downstream veins, downstream of said select locations upstream for the infusion of said cytotoxic drug.

6. The method of claim 5, further comprising using one or more dual-lumen catheters having longitudinally spaced injection and withdrawal apertures to accomplish removal and injection of blood from said veins.

7. The method of claim 1, further comprising effecting visualization of said tumor using a solution of monoclonal antibodies specific to said tumor conjugated to an imaging marker.

8. The method of claim 1, further comprising effecting visualization of blood flow within said tumor using an angiographic contrast medium.

9. The method of claim 1, further comprising predicting the pattern and concentration of dispersion of said cytotoxic drug within said tumor using potential flow modeling.

10. The method of claim 1, further comprising sealing off said arteries at locations downstream of said select locations upstream for the infusion of said cytotoxic drug.

11. The method of claim 10, wherein said arteries are sealed off by laser cauterization.

12. The method of claim 1, further comprising predicting the pattern and concentration of dispersion of said cytotoxic drug within said tumor using one or more neural networks.

13. The method of claim 1, wherein said cytotoxic drug is selected from the group consisting of alkylating agents, enzyme inhibitors, proliferation inhibitors, lytic agents, DNA synthesis inhibitors, membrane permeability modifiers, DNA intercalators and, antimetabolites.

14. The method of claim 2 or 3, wherein said vasoconstrictive drug is selected from the group consisting of catecholamines, norepinephrine, epinephrine, isoproterenol, dopamine, ephedrine phenylisopropylamines, phenylephrine, amphetamine, metraminol, methoxamine; ergot alkaloids including lysergic acid, lysergic acid diethylamine, ergonovine, methylergonavine, methysergide, ergotamine; angiotensins; and prostaglandins.

15. The method of claim 1, further comprising infusing a sensitizing agent into said tumor.

16. The method of claim 16, wherein said sensitizing agent is selected from the group consisting of radionuclides of technicium or iridium; nitroimidazoles; halogenated pyrimidines (BUdR); methylated xanthines; cytokines; interferons; lymphokines; interleukin-2; tumor necrosis factor; and transforming growth factor-beta.

17. The method of claim 1, wherein said visualizing of said tumor is accomplished by the group consisting of computerized axial tomography (CAT scanning), magnetic resonance imaging (MRI), ultrasonography, positron emission tomography (PET), single-photon emission computed tomography (SPECT), infrared sensing, X-ray imaging and microwave imaging.

* * * * *